(12) United States Patent

Vergne et al.

(10) Patent No.: US 6,753,340 B2
(45) Date of Patent: Jun. 22, 2004

(54) (4,2-DISUBSTITUTED-THIAZOL-5-YL) AMINE COMPOUNDS AS PDE7 INHIBITORS

(75) Inventors: Fabrice Vergne, Gif Sur Yvette (FR); Patrick Bernardelli, Fontenay Aux Roses (FR); Edwige Lorthiois, Paris (FR); Pierre Ducrot, Verrieres le Buisson (FR)

(73) Assignee: Warner-Lambert Company LLC, Morris Plains, NJ (US)

( * ) Notice: Subject to any disclaimer, the term of this patent is extended or adjusted under 35 U.S.C. 154(b) by 95 days.

(21) Appl. No.: 10/401,392

(22) Filed: Mar. 27, 2003

(65) Prior Publication Data

US 2003/0191167 A1 Oct. 9, 2003

(30) Foreign Application Priority Data

Mar. 28, 2002 (EP) .............................................. 02290788

(51) Int. Cl.[7] ..................... C07D 277/42; A61K 31/426

(52) U.S. Cl. ....................................... 514/370; 548/190

(58) Field of Search ........................... 514/370; 548/190

(56) References Cited

PUBLICATIONS

Katritzhy, J Org Chem 65 (23) 8077 2000.*
Ukichawa J Het Chem 31 (4) 877 1994.*
J. Pharm. Sci. 1977. 66. 1–19.

* cited by examiner

Primary Examiner—Robert Gerstl
(74) Attorney, Agent, or Firm—Peter C. Richardson; Gregg C. Benson; Robert T. Ronau

(57) ABSTRACT

A compound selected from those of formula (I):

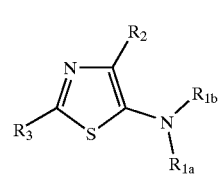

wherein $R_{1a}$, $R_{1b}$, $R_2$, $R_3$, are as defined in the description, and optionally, its optical isomers, N-oxide, and addition salts thereof with a pharmaceutically-acceptable acid or base, and medicinal products containing the same are useful as specific inhibitors of phosphodiesterase-7 (PDE-7).

19 Claims, No Drawings

(4,2-DISUBSTITUTED-THIAZOL-5-YL) AMINE COMPOUNDS AS PDE7 INHIBITORS

CROSS REFERENCE TO RELATED APPLICATIONS

This application claims the benefit of European Patent Application No. 02290788.5 filed Mar. 28, 2002.

The present invention relates to (4,2-disubstituted-thiazol-5-yl)amine derivatives, a process for their preparation, and pharmaceutical compositions containing them. These new compounds are useful as phosphodiesterase 7 (PDE7) inhibitors. Further contained in this invention are pharmaceutical compositions containing these phosphodiesterase 7 inhibitors as active principle for the treatment of disease for which treatment by PDE7 inhibitor is relevant. These medicinal products are useful in particular for treating T-cell-related diseases, autoimmune diseases, visceral pain, osteoarthritis, multiple sclerosis, osteoporosis, chronic obstructive pulmonary disease, allergic rhinitis, asthma, cancer, acquired immune deficiency syndrome, allergy, fertility diseases or inflammatory bowel disease.

Phosphodiesterases (PDE) play an important role in various biological processes by hydrolysing the key second messengers adenosine and guanosine 3',5'-cyclic monophosphates (cAMP and cGMP respectively) into their corresponding 5'-monophosphate nucleotides. Therefore, inhibition of PDE activity produces an increase of cAMP and cGMP intracellular levels that activate specific protein phosphorylation pathways involved in a variety of functional responses.

At least eleven isoenzymes of mammalian cyclic nucleotide phosphodiesterases, numbered PDE 1 through PDE 11, have been identified on the basis of primary structure, substrate specificity or sensitivity to cofactors or inhibitory drugs. Among these phosphodiesterases, PDE7 is a cAMP-specific PDE. The biochemical and pharmacological characterization showed a high-affinity cAMP-specific PDE ($Km=0.2 \mu M$), that is not affected by cGMP potent selective PDE isoenzyme inhibitors.

PDE7 activity or protein has been detected in T-cell lines, B-cell lines, airway epithelial (AE) cell lines and several foetal tissues.

Increasing cAMP levels by selective PDE7 inhibition appears to be a potentially promising approach to specifically block T-cell mediated immune responses. Further studies have demonstrated that elevation of intracellular cAMP levels can modulate inflammatory and immunological processes. This selective approach could presumably be devoid of the side effects associated with known selective PDE inhibitors (e.g. PDE3 or PDE4 selective inhibitors) and which limit their use.

A functional role of PDE7 in T-cell activation has also been disclosed; therefore selective PDE7 inhibitors would be candidates for the treatment of T-cell-related diseases. AE cells actively participate in inflammatory airway diseases by liberating mediators such as arachidonate metabolites and cytokines. Selective inhibition of PDE7 may be a useful anti-inflammatory approach for treating AE cells related diseases.

Thus, there is a need for selective PDE7 inhibitors, which are active at very low concentrations.

The applicant has identified novel (4,2-disubstituted-thiazol-5-yl)amine compounds that are phosphodiesterase inhibitors, and more specifically compounds that are selective PDE7 inhibitors.

More specifically, the present invention relates to compounds of formula (I):

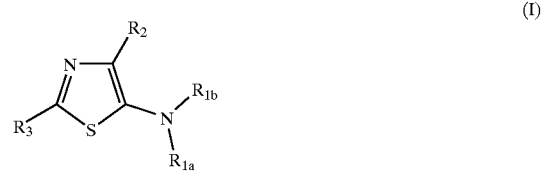

wherein:

$R_{1a}$ represents a group selected from hydrogen, ($C_1$–$C_6$) alkyl, and aryl($C_1$–$C_6$)alkyl, $R_{1b}$ represents a group selected from cycloalkyl, heterocycloalkyl, aryl and heteroaryl, those groups being optionally substituted by one or more groups, identical or different, selected independently of each other from halogen, trifluoromethyl, nitro, cyano, oxo, —$NR_4R_5$, —$CO_2R_4$, —$CONR_4R_5$, —$OR_4$, —$S(O)_nR_4$, —$S(O)_nNR_4R_5$, tetrazolyl, and ($C_1$–$C_6$)alkyl which is optionally substituted by 1 to 3 groups, identical or different, selected independently of each other from —$OR_4$, —$NR_4R_5$, and —$CO_2R_4$, wherein:

n is an integer from 0 to 2 inclusive, $R_4$ and $R_5$, identical or different, independently of each other, represent a hydrogen atom or a group of formula —$X_1$—$R_a$ wherein:

$X_1$ represents a single bond or a ($C_1$–$C_6$)alkylene group, $R_a$ represents a group selected from ($C_1$–$C_6$)alkyl, cycloalkyl, heterocycloalkyl, aryl and heteroaryl, $R_2$ represents a group selected from ($C_1$–$C_6$)alkyl, ($C_2$–$C_6$)alkenyl, ($C_2$–$C_6$)alkynyl, aryl and cycloalkyl, $R_3$ represents a group selected from cycloalkyl, heterocycloalkyl, aryl and heteroaryl, these groups being optionally substituted by one or more groups, identical or different, selected independently of each other from halogen, nitro, cyano, trifluoromethyl, oxo, ($C_1$–$C_6$)alkyl, —$OR_6$, —$NR_6R_7$, —$COR_6$, —$CO_2R_6$, —$CONHOH$, —$CONR_6R_7$, —$S(O)_mR_6$, —$S(O)_m$—$NR_6R_7$, —$NR_6COR_7$, —$NR_6SO_2R_7$, —$N(SO_2R_7)_2$, —$NR_6$—CO—$NR_7R_8$, C(=N—CN)$NR_6R_7$, $NR_8$—C(=N—CN)$NR_6R_7$ and tetrazolyl optionally substituted with a ($C_1$–$C_4$)alkyl, wherein:

m is an integer from 0 to 2 inclusive, $R_6$ and $R_7$, identical or different, independently of each other, represent a hydrogen atom or a group of formula —$X_2$—$R_b$ wherein:

$X_2$ represents a single bond or a ($C_1$–$C_6$)alkylene group, $R_b$ represents a group selected from ($C_1$–$C_6$)alkyl, cycloalkyl, heterocycloalkyl, aryl and heteroaryl, these groups being optionally substituted by 1 to 3 groups, identical or different, selected independently of each other from hydroxy, ($C_1$–$C_6$) alkoxy, ($C_1$–$C_6$)alkyl, amino, mono($C_1$–$C_6$) alkylamino, di($C_1$–$C_6$)alkylamino (each alkyl being identical or different, independently of each other), carboxy, ($C_1$–$C_6$)alkoxycarbonyl, and benzyl, $R_8$ represents a hydrogen atom or a ($C_1$–$C_6$)alkyl group, optionally the racemics forms thereof, isomers thereof, N-oxides thereof, and the pharmaceutically acceptable acid or base salts thereof.

Preferably, the present invention relates to compounds of formula (I)

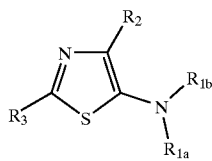

(I)

wherein $R_{1a}$, $R_{1b}$, $R_2$ and $R_3$ are as defined above, with the exclusion of the following compounds:
- (4-Methyl-2-phenyl-thiazol-5-yl)-phenyl-amine,
- (2,4-diphenyl-thiazol-5-yl)-phenyl-amine,
- (2,4-diphenyl-thiazol-5-yl)-(3-fluoro-phenyl)-amine,
- (2,4-diphenyl-thiazol-5-yl)-(4-fluoro-phenyl)-amine,
- (4-chloro-phenyl)-(2,4-diphenyl-thiazol-5-yl)-amine,
- (2-chloro-phenyl)-(2,4-diphenyl-thiazol-5-yl)-amine,
- (2,4-diphenyl-thiazol-5-yl)-p-tolyl-amine, and,
- (2,4-diphenyl-thiazol-5-yl)-(4-methoxy-phenyl)-amine.

Preferably, the present invention relates to compounds of formula (I)

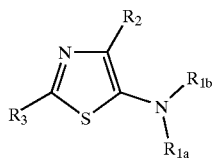

(I)

wherein $R_{1a}$, $R_{1b}$, $R_2$ and $R_3$ are as defined above, with the exclusion of the following compounds:
- (4-Methyl-2-phenyl-thiazol-5-yl)-phenyl-amine,
- (2,4-diphenyl-thiazol-5-yl)-phenyl-amine,
- (2,4-diphenyl-thiazol-5-yl)-(3-fluoro-phenyl)-amine,
- (2,4-diphenyl-thiazol-5-yl)-(4-fluoro-phenyl)-amine,
- (4-chloro-phenyl)-(2,4-diphenyl-thiazol-5-yl)-amine,
- (2-chloro-phenyl)-(2,4-diphenyl-thiazol-5-yl)-amine,
- (2,4-diphenyl-thiazol-5-yl)-p-tolyl-amine, and,
- (2,4-diphenyl-thiazol-5-yl)-(4-methoxy-phenyl)-amine,
- and with the proviso that $R_{1b}$ is other than a substituted pyrimidine or a substituted pyrimidine fused to one or several other cycles.

The substituent $R_{1a}$ that is preferred according to the invention is the hydrogen atom or a ($C_1$–$C_6$)alkyl group, and the substituent $R_{1b}$ that is preferred according to the invention is the group selected from cycloalkyl and aryl, each of those groups being optionally substituted by 1 to 3 groups selected from halogen, trifluoromethyl, —$CO_2R_4$, —$OR_4$, and tetrazolyl, in which $R_4$ represents a hydrogen atom or a ($C_1$–$C_6$)alkyl group.

More particularly, the substituent $R_{1a}$ that is preferred according to the invention is the hydrogen atom, and the substituent $R_{1b}$ that is preferred according to the invention is the cyclohexyl group optionally substituted by one hydroxy group, or the phenyl group optionally substituted by one tetrazolyl group or one —$CO_2R_4$ group in which $R_4$ represents a hydrogen atom or a ($C_1$–$C_6$)alkyl group.

The substituent $R_2$ that is preferred according to the invention is a ($C_1$–$C_6$)alkyl group.

More particularly, the substituent $R_2$ that is preferred according to the invention is the methyl group.

The substituent $R_3$ that is preferred according to the invention is a group selected from aryl and heteroaryl which are optionally substituted by one to three groups, identical or different, independently of each other, as defined in the general definition of compounds of formula (I).

More particularly, the substituent $R_3$ that is preferred according to the invention is a group selected from phenyl, pyridyl, thienyl, isoxazolyl, pyrazolyle, pyrazinyl, quinolyl, quinoxalinyl, 1H-quinoxalinyl-2-one, quinazolinyl, 3H-quinazolinyl-4-one, 1H-quinazolinyl-2,4-dione, indolyle, benzisoxazolyl, phtalazinyl, and benzo[1,3]dioxolyle, which are optionally substituted by one to three groups, identical or different, independently of each other, as defined in the general definition of compounds of formula (I).

As a preferred embodiment, the substituent $R_3$ that is particularly interesting for the invention is the phenyl group substituted by one to three groups, identical or different, selected independently of each other from halogen, —$OR_6$, —$CO_2R_6$, —$CONR_6R_7$, —$S(O)_mR_6$, —$S(O)_m$—$NR_6R_7$, —$NR_6COR_7$, and tetrazolyl, wherein:
  m is an integer from 0 to 2 inclusive,
  $R_6$ and $R_7$, identical or different, independently of each other, represent a hydrogen atom or a group of formula —$X_2$—$R_b$ wherein:
    $X_2$ represents a single bond or a ($C_1$–$C_6$)alkylene group,
    $R_b$ represents a group selected from ($C_1$–$C_6$)alkyl, cycloalkyl, heterocycloalkyl, aryl and heteroaryl, these groups being optionally substituted by 1 to 3 groups, identical or different, selected independently of each other from hydroxy, ($C_1$–$C_6$)alkoxy, ($C_1$–$C_6$)alkyl, amino, mono($C_1$–$C_6$)alkylamino, di($C_1$–$C_6$)alkylamino (each alkyl being identical or different, independently of each other), carboxy, ($C_1$–$C_6$)alkoxycarbonyl, and benzyl.

In an another preferred embodiment, the substituent $R_3$ that is particularly interesting for the invention is the group selected from quinoxalinyl, 1H-quinoxalinyl-2-one, quinazolinyl, 3H-quinazolinyl-4-one, and 1H-quinazolinyl-2,4-dione, which are optionally substituted by one to three groups, identical or different, selected independently of each other from halogen, ($C_1$–$C_6$)alkyl, $OR_6$, and $NR_6R_7$, wherein:
  $R_6$ and $R_7$, identical or different, independently of each other, represent a hydrogen atom or a group of formula —$X_2$—$R_b$ wherein:
    $X_2$ represents a single bond
    $R_b$ represents a group ($C_1$–$C_6$)alkyl, which is optionally substituted by one group selected from hydroxy, ($C_1$–$C_6$)alkoxy, amino, mono($C_1$–$C_6$)alkylamino, and di($C_1$–$C_6$)alkylamino (each alkyl amino being identical or different, independently of each other).

According to a first embodiment, the invention relates to compounds of formula (I) wherein:
  $R_{1a}$ represents a hydrogen atom,
  $R_{1b}$ represents a cyclohexyl group optionally substituted by one hydroxy group, or a phenyl group optionally substituted by one tetrazolyl group or one —$CO_2R_4$ group in which R4 represents a hydrogen atom or a ($C_1$–$C_6$)alkyl group,
  $R_2$ represents a methyl group,
  $R_3$ represents a phenyl group substituted by one to three groups, identical or different, selected independently of each other from halogen, —$OR_6$, —$CO_2R_6$, —$CONR_6R_7$, —$S(O)_mR_6$, —$S(O)_m$—$NR_6R_7$, —$NR_6COR_7$, and tetrazolyl, wherein:

m is an integer from 0 to 2 inclusive, $R_6$ and $R_7$, identical or different, independently of each other, represent a hydrogen atom or a group of formula —$X_2$—$R_b$ wherein:

$X_2$ represents a single bond or a ($C_1$–$C_6$)alkylene group, $R_b$ represents a group selected from ($C_1$–$C_6$)alkyl, cycloalkyl, heterocycloalkyl, aryl and heteroaryl, these groups being optionally substituted by 1 to 3 groups, identical or different, selected independently of each other from hydroxy, ($C_1$–$C_6$)alkoxy, ($C_1$–$C_6$)alkyl, amino, mono($C_1$–$C_6$)alkylamino, di($C_1$–$C_6$)alkylamino (each alkyl amino being identical or different, independently of each other), carboxy, ($C_1$–$C_6$)alkoxycarbonyl, and benzyl.

According to a second embodiment, the invention relates to compounds of formula (I) wherein:

$R_{1a}$ represents a hydrogen atom, $R_{1b}$ represents a cyclohexyl group optionally substituted by one hydroxy group, or a phenyl group optionally substituted by one tetrazolyl group or one —$CO_2R_4$ group in which $R_4$ represents a hydrogen atom or a ($C_1$–$C_6$)alkyl group, $R_2$ represents a methyl group, $R_3$ represents a group selected from quinoxalinyl, 1H-quinoxalinyl-2-one, quinazolinyl, 3H-quinazolinyl-4-one, 1H-quinazolinyl-2,4-dione, which are optionally substituted by one to three groups, identical or different, selected independently of each other from halogen, ($C_1$–$C_6$)alkyl, —$OR_6$, and —$NR_6R_7$, wherein $R_6$ and $R_7$, identical or different, independently of each other, represent a hydrogen atom or a group of formula —$X_2$—$R_b$ wherein:

$X_2$ represents a single bond, $R_b$ represents a ($C_1$–$C_6$)alkyl group, which is optionally substituted by one group selected from hydroxy, ($C_1$–$C_6$)alkoxy, amino, mono($C_1$–$C_6$)alkylamino, and di($C_1$–$C_6$)alkylamino (each alkyl amino being identical or different, independently of each other).

The preferred compounds of the invention are:

N-{4-[5-(cyclohexylamino)-4-methyl-1,3-thiazol-2-yl]phenyl}acetamide,

N-{4-[5-[(3-hydroxycyclohexyl)amino]-4-methyl-1,3-thiazol-2-yl]phenyl}acetamide, 7-[5-(cyclohexylamino)-4-methyl-1,3-thiazol-2-yl]quinazolin-4-amine, and 7-{5-[(3-hydroxycyclohexyl)amino]-4-methyl-1,3-thiazol-2-yl}quinazolin-4-amine.

The optical isomers, the N-oxides, as well as the addition salts with a pharmaceutically acceptable acid or base, of the preferred compounds form an integral part of the invention.

The compounds provided by this invention are those defined in formula (I). In formula (I), it is understood that:

a ($C_1$–$C_6$)alkyl group denotes a linear or branched group containing from 1 to 6 carbon atoms; example of such groups, without implying any limitation are methyl, ethyl, propyl, isopropyl, tert-butyl, neopentyl, hexyl, . . .

a ($C_1$–$C_6$)alkylene group denotes a ($C_1$–$C_6$)alkyl group as defined hereinbefore which is comprised between two groups; example of such groups, without implying any limitation are methylene (—($CH_2$)—), ethylene (—($C_2$)$_2$—), . . .

a ($C_2$–$C_6$)alkenyl group denotes a linear or branched group containing from 2 to 6 carbon atoms, and one or more carbon—carbon double bonds; examples of such groups without implying any limitation are vinyl, allyl, 3-buten-1-yl, 2-methyl-buten-1-yl, hexenyl, . . .

a ($C_2$–$C_6$)alkynyl group denotes a linear or branched group containing from 2 to 6 carbon atoms, and one or more carbon—carbon triple bonds; examples of such groups without implying any limitation are ethynyl, propynyl, 3-butyn-1-yl, 2-methyl-butyn-1-yl, hexynyl, . . .

a ($C_1$–$C_6$)alkoxy group means the alkyl group as mentioned above bound through an oxygen atom; examples of such groups without implying any limitation are methoxy, ethoxy, n-propyloxy, tert-butyloxy, . . .

a mono($C_1$–$C_6$)alkylamino denotes an amino group substituted by one ($C_1$–$C_6$)alkyl group as defined hereinbefore; example of such groups, without implying any limitation are methylamino, isobutylamino, ethylamino, . . .

a di($C_1$–$C_6$)alkylamino denotes an amino group substituted by two ($C_1$–$C_6$)alkyl groups as defined hereinbefore, each alkyl group being identical or different independently of each other; example of such groups, without implying any limitation are dimethylamino, diethylamino, methylethylamino, an aryl group denotes an aromatic monocyclic or bicyclic system containing from 5 to 10 carbon atoms, and in the case of a bicyclic system, one of the ring of which is aromatic in character, and the other ring of which may be aromatic or partially hydrogenated and it being understood that in the case of a bicyclic system when the second ring is partially hydrogenated then it may be optionally substituted by one or two oxo groups; examples of such groups without implying any limitation are, phenyl, naphthyl, indenyl, benzocyclobutenyl, benzocylohexyl, benzocyclohex-3enyl, benzocyclopentyl, benzocyclohexyl-1-one, . . .

a heteroaryl group denotes an aryl group as described above in which 1 to 4 carbon atoms are replaced by 1 to 4 hetero atoms, identical or different, selected independently of each other from oxygen, sulfur and nitrogen; examples of such groups without implying any limitation are furyl, thienyl, pyrrolyl, pyrazolyl, pyridyl, pyrimidyl, pyrazinyl, benzofuryl, benzothienyl, indolyl, quinolyl, isoquinolyl, benzisoxazolyl, phtalazinyl, benzodioxolyl, benzodioxinyl, benzo[1,2,5]thiadiazolyl, benzo[1,2,5]oxadiazolyl, benzopyrrolinyl, quinoxalinyl, 1H-quinoxalinyl, quinazolinyl, 3H-quinazolinyl-4-one, 1H-quinzolinyl-2,4-dione, . . .

a cycloalkyl group denotes a monocyclic or polycyclic system containing from 3 to 10 carbon atoms, this system being saturated or partially unsaturated but without aromatic character and it being understood that in the case of a polycyclic system each cycle could be fused together or form a link; examples of such groups without implying any limitation are cyclopropyl, cyclobutyl, cyclopentyl, cyclohexyl, cyclooctyl, cycloheptyl, adamantyl, decalinyl, norbornyl, cyclo[2,2,1]heptyl, cyclo[2,2,2]octyl . . .

a heterocycloalkyl group denotes a cycloalkyl group as defined hereinbefore in which 1 to 4 carbon atoms are replaced by 1 to 4 hetero atoms, identical or different selected independently of each other from oxygen, sulfur, and nitrogen, a acyl group denotes a ($C_1$–$C_6$)alkyl group or an aryl group as defined above bound through a carbonyl group; examples of such groups without implying any limitation are acetyl, ethylcarbonyl, benzoyl, ...

a $(C_1-C_6)$alkoxycarbonyl denotes a $(C_1-C_6)$alkoxy group as defined hereinbefore bound through a carbonyl group; examples of such groups without implying any limitation are methoxycarbonyl, ethoxycarbonyl, tert-butyloxycarbonyl, ...

optical isomers refer to racemates, enantiomers and diastercoisomers.

The invention also relates to the pharmaceutically acceptable salts of the compounds of formula (I). A review of the pharmaceutically acceptable salts will be found in *J. Pharm. Sci.*, 1977, 66, 1–19.

Pharmaceutically acceptable acids mean non-toxic mineral or organic acids. Among those there may be mentioned, without implying any limitation, hydrochloric acid, hydrobromic acid, sulfuric acid, phosphonic acid, nitric acid, citric acid, acetic acid, trifluoroacetic acid, lactic acid, pyruvic acid, malonic acid, succinic acid, glutaric acid, fumaric acid, tartaric acid, maleic acid, ascorbic acid, oxalic acid, methanesulfonic acid, camphoric acid, benzoic acid, toluenesulfonic acid, etc. . .

Pharmaceutically acceptable bases mean non-toxic mineral or organic bases. Among those, there may be mentioned, without implying any limitation, sodium hydroxide, potassium hydroxide, calcium hydroxide, triethylamine, tert-butylamine, dibenzylethylenediamine, piperidine, pyrrolidine, benzylamine, quaternary ammonium hydroxides, etc. . .

The invention also relates to a process for the preparation of compounds of formula (I), which uses as starting material a compound of formula (II):

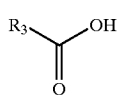
(II)

wherein $R_3$ is as defined in the compound of formula (I), compound of formula (II) reacting under peptidic coupling conditions with a compound of formula (III):

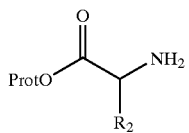
(III)

wherein $R_2$ is as defined in the compound of formula (I), and Prot represents a protective group of carboxylic group usually used in organic synthesis, like for example and without any limitation a methyl group or a tert-butyl group, to give the compound of formula (IV):

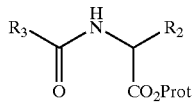
(IV)

wherein $R_2$, $R_3$ and Prot are as defined hereinbefore, compound of formula (IV) being deprotected in a first step by treatment with an acid or a base depending on the nature of the protecting group, to give the corresponding free carboxylic acid compound of formula (V):

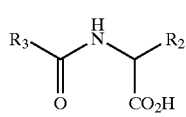
(V)

wherein $R_2$ and $R_3$ are as defined hereinbefore, and then in a second step reacting in peptidic coupling condition, using a coupling agent like for example dicyclohexylcarbodiimide or 1,1'-carbonyldiimidzole, and a primary amine of formula (VI):

$R_{1b}-NH_2$ (VI)

wherein $R_{1b}$ is as defined in the compound of formula (I), to give the compound of formula (VII):

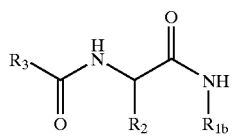
(VII)

wherein $R_{1b}$, $R_2$ and $R_3$ are as defined hereinbefore, compound of formula (VII) being treated with Lawesson's reagent in basic medium, for example using pyridine, to give the compound of formula (I/a), which is a particular case of compounds of formula (I):

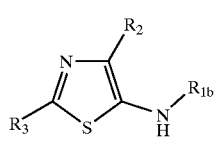
(I/a)

in which $R_{1b}$, $R_2$ and $R_3$ are as defined hereinbefore, compound of formula (I/a) being treated optionally under alkaline medium, with a compound of formula (VIII):

$R_{1a'}-L_1$ (VIII)

wherein $R_{1a'}$ has the same definition of the group $R_{1a}$ in the compound of formula (I) except the definition of hydrogen atom, and $L_1$ represents a leaving group like for example and without any limitations, chloride, bromide, iodide, tosylate, triflate or mesylate group, to give the compound of formula (I/b) which is a particular case of compounds of formula (I):

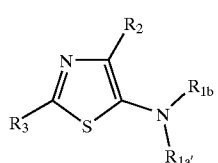
(I/b)

in which $R_{1a'}$, $R_{1b}$, $R_2$ and $R_3$ are as defined hereinbefore, compounds of formulae (I/a) and (I/b) constitute compounds of the invention, which are purified, where appropriate, according to a conventional purification technique, which are separated, where appropriate, into their different isomers according to a conventional separation technique, and which are converted, where appropriate, into addition salts thereof with a pharmaceutically acceptable acid or base, or into N-oxide thereof.

The compounds of formulae (II), (III), (VI) and (VIII) are commercially available or are obtained easily by using classical reactions of organic synthesis well known by the man skilled in the art.

The compounds of the invention that are present in the form of a mixture of diastereoisomers are isolated in a pure form by using conventional separation techniques such as chromatography.

As mentioned above, compounds of formula (I) of the present invention are phosphosdiesterase inhibitors, and more particularly inhibitors of the enzyme PDE7.

The present invention also relates to pharmaceutical compositions comprising as active ingredient at least one compound of formula (I), an isomer thereof, a N-oxide thereof, or an addition salt thereof with a pharmaceutically acceptable acid or base, alone or in combination with one or more pharmaceutically acceptable, inert, non-toxic excipients or carriers.

The invention also relates to a pharmaceutical composition comprising as active principle an effective amount of a compound of formula (I) alone or in combination with one or more pharmaceutically acceptable excipients or carriers. This pharmaceutical composition is useful for the treatment of a disease for which treatment by PDE7 inhibitor is relevant.

More particularly, the pharmaceutical composition described above is useful for treating a pathology in which the disease to be treated is selected from T-cell-related diseases, autoimmune diseases, inflammatory diseases, respiratory diseases, CNS diseases, allergic diseases, endocrine or exocrine pancreas diseases, and gastrointestinal diseases.

In a preferred embodiment the pharmaceutical composition is useful to treat a disease which is selected from visceral pain, inflammatory bowel disease, osteoarthritis, multiple sclerosis, osteoporosis, chronic obstructive pulmonary disease (COPD), allergic rhinitis, asthma, cancer, acquired immune deficiency syndrome (AIDS) and graft rejection.

Among the pharmaceutical compositions according to the invention, there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

Pharmaceutical compositions according to the invention for parenteral injections especially include aqueous and non-aqueous sterile solutions, dispersions, suspension and emulsions, and also sterile powders for reconstituting injectable solutions or dispersions.

Pharmaceutical compositions according to the invention for oral administration in solid form especially include tablets or dragées, sublingual tablets, sachets, gelatin capsules and granules, for oral, nasal, buccal or ocular administration in liquid form, especially include emulsions, solutions, suspensions, drop, syrups and aerosols.

Pharmaceutical compositions for rectal or vaginal administration are preferably suppositories, and those for per- or trans-cutaneous administration especially include powders, aerosols, creams, ointment, gels and patches.

The pharmaceutical compositions mentioned hereinbefore illustrate the invention but do not limit it in any way.

Among the pharmaceutically acceptable, inert, non-toxic excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colorants, aromatizing agents etc. . .

The useful dosage varies according to the age and weight of the patient, the administration route, the pharmaceutical composition used, the nature and severity of the disorder and the administration of any associated treatments. The dosage ranges from 1 mg to 1 g per day in one or more administrations. The compositions are prepared by methods that are common to those skilled in the art and generally comprise 0.5% to 80% by weight of active principle (compound of formula (I)) and 20% to 99.5% by weight of pharmaceutically acceptable excipients or carriers.

The compounds of the invention are PDE inhibitors, and particularly PDE7 inhibitors.

Preferably, the compounds of the invention are selective PDE7 inhibitors. "Selective PDE7 inhibitors" refers to compounds which have an $IC_{50}$ for PDE7 at least 5 times lower than the $IC_{50}$ for a PDE distinct from PDE7, and preferably at least 10 times, 15 times, 20 times, 30 times, 40 times, 50 times or 100 times lower than the $IC_{50}$ value for a PDE distinct from PDE7.

A PDE distinct from PDE7 refers preferably to a PDE chosen from PDE1, PDE3, PDE4 or PDE5.

The examples that follow illustrate the invention but do not limit it in any way. The compounds described in these examples could be obtained by the following synthetic ways.

The starting materials used are products that are known or that are prepared according to known operating procedures.

The reactions are monitored by tin layer chromatography (T.L.C.).

The structures of the compounds described in the Examples are determined according to the usual spectrophotometric techniques (infrared, nuclear magnetic resonance, mass spectrometry, . . . ).

EXAMPLES

Example 1

N-{4-[5-(cyclohexylamino)-4-methyl-1,3-thiazol-2-yl]phenyl}acetamide

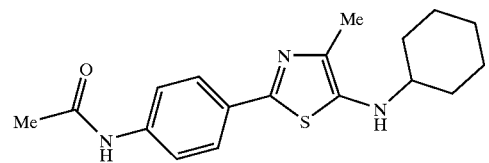

Step 1:
tert-Butyl(2S)-2-[(4-nitrobenzoyl)amino]-propanoate

To a solution of para-nitrobenzoic acid in tetrahydrofuran, 1.2 equivalents of 1,1'-carbonyldiumidazole are added and the mixture is stirred for 30 minutes. Then, 1.1 equivalents of the (S)-L-alanine tert-butyl ester are added and the mixture is stirred for 24 hours at room temperature. The solvent is removed under reduced pressure and the crude is diluted in chloroform and brine. The organic layer is washed with water and dried over $MgSO_4$. The filtrate is concentrated under vacuum and the residue is purified by column chromatography to give the desired compound.

Step 2:
(2S)-2-[(4-Nitrobenzoyl)amino]-propanoic acid

The compound obtained in the preceding Step 1 is added to a solution of 5% of trifluoroacetic acid in dichloromethane and the mixture is stirred for 3 hours until reaction completion. Then, the solvent is distilled under reduced pressure. The crude is washed several times with toluene and then used without further purification in the next step.

Step 3:
N-[(1S)-2-(cyclohexylamino)-1-methyl-2-oxoethyl]-4-nitrobenzamide

To a solution of the compound, obtained in the preceding Step 2, in tetrahydrofuran, 1.2 equivalents of 1,1'-carbonyldiimidazole are added and the mixture is stirred for 30 minutes. Then, the cyclohexylamine is added and the mixture is stirred for 24 hours at room temperature. The solvent is removed under reduced pressure and the crude is diluted in chloroform and brine. The organic layer is washed with water and dried over $MgSO_4$. The filtrate is concentrated and the residue is purified by column chromatography to give the desired product.

Step 4:
N-cyclohexyl-4-methyl-2-(4-nitrophenyl)-1,3-thiazol-5-amine

To a solution of the compound, obtained in the preceding Step 3, in pyridine is added Lawesson's reagent and the mixture is heated at 100° C. for 6 hours until disappearance of starting material. After being cooled to room temperature, saturated aqueous sodium hydrogen carbonate solution is added to the reaction mixture, and the product is extracted with chloroform/methanol. The organic layer is washed with water and brine, and dried over $MgSO_4$. The filtrate is concentrated and the residue is purified by column chromatography to give the desired product.

Step 5:
2-(4-Aminophenyl)-N-cyclohexyl-4-methyl-1,3-thiazol-5-amine

Tin chloride dihydrate is added to a solution of the compound, obtained in the preceding Step 4, in ethanol at 70° C. and the mixture is refluxed for 3 hours until disappearance of starting material. The mixture is then filtered through a pad of celite and the filtrate is evaporated to dryness. The crude material is basified with a saturated solution of sodium bicarbonate then extracted with ethyl acetate. The organic layer is washed with water and brine, dried over $MgSO_4$, filtered and evaporated to dryness. The residue is chromatographied through silica gel to give the pure desired product.

Step 6:
N-{4-[5-(cyclohexylamino)-4-methyl-1,3-thiazol-2-yl]phenyl}acetamide

To a solution of the compound, obtained in the preceding Step 5, and triethylamine (1.1 equivalents) in tetrahydrofuran at 0° C., 1 equivalent of acetyl chloride is added and after 15 minutes of stirring the mixture is allowed to warm-up to room temperature for 5 hours until reaction completion. The mixture is concentrated under reduced pressure and the residue is purified by chromatography on silica gel to give the expected compound.

Example 2
7-[5-(Cyclohexylamino)-4-methyl-1,3-thiazol-2-yl]quinazolin-4-amine

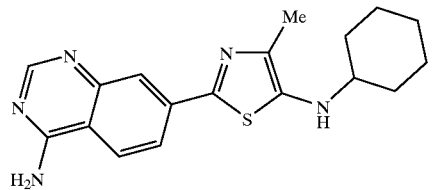

Step 1:
tert-Butyl (2S)-2-{[(4-oxo-3,4-dihydroquinazolin-7-yl)carbonyl]amino}propanoate To a solution of 4-oxo-3,4-dihydro-quinazoline-7-carboxylic acid in tetrahydrofuran, 1.2 equivalents of 1,1'-carbonyldiimidazole are added and the mixture is stirred for 30 minutes. Then, the (S)-L-Alanine tert-butyl ester is added and the mixture is stirred for 24 hours until disappearance of starting material. The solvent is removed under reduced pressure and the crude is diluted in chloroform and brine. The organic layer is washed with water and dried over $MgSO_4$. The filtrate is concentrated and the residue is purified by column chromatography to give the desired compound.

Step 2:
(2S)-2-{[(4-Oxo-3,4-dihydroquinazolin-7-yl)carbonyl]amino}propanoic acid The compound, obtained in the preceding Step 1, is added to a solution of 5% trifluoroacetic acid in dichloromethane and the mixture is stirred for 3 hours until reaction completion. Then, the solvent is distilled under reduced pressure. The crude is washed several times with toluene and then used without further purification in the next step.

Step 3:
N-[(1S)-2-(Cyclohexylamino)-1-methyl-2-oxoethyl]-4-oxo-3,4-dihydroquinazoline-7-carboxamide To a solution of the compound, obtained in the preceding Step 2, in tetrahydrofuran, 1.2 equivalents of 1,1'-carbonyldiimidazole are added and the mixture is stirred for 30 minutes. Then, the cyclohexylamine is added and the mixture is stirred for 24 hours until disappearance of starting material. The solvent is removed under reduced pressure and the crude is diluted in chloroform and brine. The organic layer is washed with water and dried over $MgSO_4$. The filtrate is concentrated and the residue is purified by column chromatography to give the desired compound.

Step 4:
7-[5-(Cyclohexylamino)-4-methyl-1,3-thiazol-2-yl]quinazoline-4(3H)-thione To a solution of the compound, obtained in the preceding Step 3, in pyridine is added Lawesson's reagent and the mixture is heated to 100° C. for 6 hours until disappearance of starting material. After being cooled to room temperature, saturated aqueous sodium hydrogen carbonate solution is added to the reaction mixture, and the product is extracted with chloroform/methanol. The organic layer is washed with water and brine, and dried over $MgSO_4$. The filtrate is concentrated and the residue is purified by column chromatography to give the desired compound.

Step 5:
N-cyclohexyl-4-methyl-2-[4-(methylthio)quinazolin-7-yl]-1,3-thiazol-5-amine To a stirring solution of the compound, obtained in the preceding Step 4, and potassium carbonate (1.2 equivalents) in methanol is added methyl iodide. After 30 minutes the solvent is removed by rotary evaporation and the residue purified via column chromatography to give a powder corresponding to the desired compound.

Step 6:
7-[5-(Cyclohexylamino)-4-methyl-1,3-thiazol-2-yl]quinazolin-4-amine

A solution of the compound, obtained in the preceding Step 5, in saturated butanolic amonnia is sealed in a steel bomb and heated at 100° C. for 2 days. The solvent is removed by rotary evaporation and the residue purified via column chromatography to give the title compound.

Example 3
Biological Results/In Vitro Inhibition of the Phosphodiesterase 7 and of Other Phosphodiesterases The capacity of the compounds of the invention to inhibit cyclic nucleotide phosphodiesterases is evaluated by measuring their $IC_{50}$ (concentration necessary to inhibit the enzymatic activity by 50%).

PDE3A3, PDE4D3, PDE7A1 are cloned and expressed in insect cells Sf21 using the baculovirus expression system and we uses directly the cell culture supernatant as enzyme source. The sources of PDE1 and of PDE5 are human cell lines (respectively TPH1 human monocytes and MCF7 human caucasian breast adenocarcinoma).

They are obtained partially purified on an anion exchange column (Mono Q) according to a method adapted from Lavan B. E., Lakey T., Houslay M. D. Biochemical Pharmacology, 1989, 38 (22), 4123–4136.

Measurement of the enzymatic activity for the various types of PDE is then made according to a method adapted from W. J. Thompson et al. 1979, Advances in Cyclic Nucleotide Research, Vol.10: 69–92, ed. G. Brooker et al. Raven Press, NY.

The substrate used is cGMP for PDE1 and PDE5 and cAMP for PDE 3, PDE 4 and PDE 7. The substrate concentration is 0.2 µM for PDE 1, PDE 3 and PDE 5, 0,25 µM for PDE 4 and 50 nM for PDE 7.

The enzymatic reaction is stopped after 1 hour for PDE 1, PDE 3 and PDE 5 and 10 minutes for PDE 4 and PDE 7.

In order to determine their $IC_{50}$, compounds of the invention are assayed at 8 to 11 concentrations ranging from 0.02 nM to 100 µM for PDE 4 and PDE 7 and at least at 6 concentrations ranging from 0.1 µM to 30 µM for PDE 1, 3 and 5.

What is claimed is:

1. A compound of formula (I):

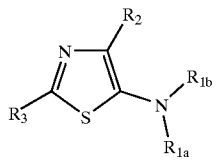

(I)

wherein:
R$_{1a}$ is a group selected from hydrogen, (C$_1$–C$_6$)alkyl and aryl(C$_1$–C$_6$)alkyl,
R$_{1b}$ is a group selected from cycloalkyl, heterocycloalkyl, aryl and heteroaryl, those groups being optionally substituted by one or more groups, identical or different, selected independently of each other from halogen, trifluoromethyl, nitro, cyano, oxo, —NR$_4$R$_5$, —CO$_2$R$_4$, —CONR$_4$R$_5$, —OR$_4$, —S(O)$_n$R$_4$, —S(O)$_n$NR$_4$R$_5$, tetrazolyl, and (C$_1$–C$_6$)alkyl which is optionally substituted by 1 to 3 groups, identical or different, selected independently of each other from —OR$_4$, —NR$_4$R$_5$, and —CO$_2$R$_4$, wherein:
n is an integer from 0 to 2 inclusive,
R$_4$ and R$_5$ are identical or different and independently of each other are a hydrogen atom or a group of formula —X$_1$—R$_a$, wherein:
X$_1$ is a single bond or a (C$_1$–C$_6$)alkylene group,
R$_a$ is a group selected from (C$_1$–C$_6$)alkyl, cycloalkyl, heterocycloalkyl, aryl and heteroaryl,
R$_2$ is a group selected from (C$_1$–C$_6$)alkyl, (C$_2$–C$_6$)alkenyl, (C$_2$–C$_6$)alkynyl, aryl and cycloalkyl,
R$_3$ is a group selected from cycloalkyl, heterocycloalkyl, aryl and heteroaryl, these groups being optionally substituted by one or more groups, identical or different, selected independently of each other from halogen, nitro, cyano, trifluoromethyl, oxo, (C$_1$–C$_6$)alkyl, —OR$_6$, —NR$_6$R$_7$, —COR$_6$, —CO$_2$R$_6$, —CONHOH, —CONR$_6$R$_7$, —S(O)$_m$R$_6$, —S(O)$_m$—NR$_6$R$_7$, —NR$_6$COR$_7$, —NR$_6$SO$_2$R$_7$, —N(SO$_2$R$_7$)$_2$, —NR$_6$—CO—NR$_7$R$_8$, C(=N—CN)NR$_6$R$_7$, NR$_8$—C(=N—CN)NR$_6$R$_7$ and tetrazolyl optionally substituted with a (C$_1$–C$_4$)alkyl, wherein:
m is an integer from 0 to 2 inclusive,
R$_6$ and R$_7$ are identical or different and independently of each other are a hydrogen atom or a group of formula —X$_2$—R$_b$ wherein:
X$_2$ is a single bond or a (C$_1$–C$_6$)alkylene group,
R$_b$ is a group selected from (C$_1$–C$_6$)alkyl, cycloalkyl, heterocycloalkyl, aryl and heteroaryl, these groups being optionally substituted by 1 to 3 groups, identical or different, selected independently of each other from hydroxy, (C$_1$–C$_6$)alkoxy, (C$_1$–C$_6$) alkyl, amino, mono(C$_1$–C$_6$)alkylamino, di(C$_1$–C$_6$) alkylamino (each alkyl amino being identical or different, independently of each other), carboxy, (C$_1$–C$_6$)alkoxycarbonyl, and benzyl,
R$_8$ is a hydrogen atom or a (C$_1$–C$_6$)alkyl group,
a racemic form thereof, an isomer thereof, an N-oxide thereof or a pharmaceutically acceptable acid or base salt thereof, provided that
(4-methyl-2-phenyl-thiazol-5-yl)-phenyl-amine,
(2,4-diphenyl-thiazol-5-yl)-phenyl-amine,
(2,4-diphenyl-thiazol-5-yl)-(3-fluoro-phenyl)-amine,
(2,4-diphenyl-thiazol-5-yl)-(4-fluoro-phenyl)-amine,
(4-chloro-phenyl)-(2,4-diphenyl-thiazol-5-yl)-amine,
(2-chloro-phenyl)-(2,4-diphenyl-thiazol-5-yl)-amine,
(2,4-diphenyl-thiazol-5-yl)-p-tolyl-amine and
(2,4-diphenyl-thiazol-5-yl)-(4-methoxy-phenyl)-amine
are excluded.

2. A compound of claim 1 wherein Rib is other than a substituted pyrimidine or a substituted pyrimidine fused to one or several other cycles.

3. A compound of claim 1 wherein:
R$_{1a}$ is a hydrogen atom or a (C$_1$–C$_6$)alkyl group,
R$_{1b}$ is a group selected from cycloalkyl and aryl, each of these groups being optionally substituted by 1 to 3 groups selected from halogen, trifluoromethyl, —CO$_2$R$_4$, —OR$_4$, and tetrazolyl, in which R$_4$ is a hydrogen atom or a (C$_1$–C$_6$)alkyl group, a racemic form thereof, an isomer thereof, an N-oxide thereof or a pharmaceutically acceptable acid or base salt thereof.

4. A compound of claim 1 wherein:
R$_{1a}$ is a hydrogen atom,
R$_{1b}$ is:
a cyclohexyl group optionally substituted by one hydroxy group,
or a phenyl group optionally substituted by one tetrazolyl group or one —CO$_2$R$_4$ in which R$_4$ is a hydrogen atom or a (C$_1$–C$_6$)alkyl group,
a racemic form thereof, an isomer thereof, an N-oxide thereof or a pharmaceutically acceptable acid or base salt thereof.

5. A compound of claim 1 wherein R$_2$ is a (C$_1$–C$_6$)alkyl group,
a racemic form thereof, an isomer thereof, an N-oxide thereof or a pharmaceutically acceptable acid or base salt thereof.

6. A compound of claim 1 wherein R$_2$ is a methyl group,
a racemic form thereof, an isomer thereof, an N-oxide thereof or a pharmaceutically acceptable acid or base salt thereof.

7. A compound of claim 1 wherein $R_3$ is a group selected from aryl and heteroaryl which are optionally substituted by one to three groups, identical or different, selected independently of each other from halogen, nitro, cyano, trifluoromethyl, oxo, $(C_1-C_6)$alkyl, —$OR_6$, —$NR_6R_7$, —$COR_6$, —$CO_2R_6$, —CONHOH, —$CONR_6R_7$, —$S(O)_mR_6$, —$S(O)_m$—$NR_6R_7$, —$NR_6COR_7$, —$NR_6SO_2R_7$, —$N(SO_2R_7)_2$, —NR—CO—$NR_7R_8$ and tetrazolyl, wherein:

m is an integer from 0 to 2 inclusive, $R_6$ and $R_7$ are identical or different and independently of each other are a hydrogen atom or a group of formula —$X_2'R_b$ wherein:

$X_2$ is a single bond or a $(C_1-C_6)$alkylene group, $R_b$ is a group selected from $(C_1-C_6)$alkyl, cycloalkyl, heterocycloalkyl, aryl and heteroaryl, these groups being optionally substituted by 1 to 3 groups, identical or different, selected independently of each other from hydroxy, $(C_1-C_6)$alkoxy, $(C_1-C_6)$alkyl, amino, mono$(C_1-C_6)$alkylamino, di$(C_1-C_6)$alkylamino (each alkyl amino being identical or different, independently of each other), carboxy, $(C_1-C_6)$alkoxycarbonyl, and benzyl, $R_8$ is a hydrogen atom or a $(C_1-C_6)$alkyl group;

a racemic form thereof, an isomer thereof, an N-oxide thereof or a pharmaceutically 10 acceptable acid or base salt thereof.

8. A compound of claim 1 wherein $R_3$ is a group selected from phenyl, pyridyl, thienyl, isoxazolyl, pyrazolyle, pyrazinyl, quinolyl, quinoxalinyl, 1H-quinoxalinyl-2-one, quinazolinyl, 3H-quinazolinyl-4-one, 1H-quinazolinyl-2,4-dione, indolyle, benzisoxazolyl, phtalazinyl, and benzo[1,3]dioxolyle, which are optionally substituted by one to three groups, identical or different, selected independently of each other from halogen, nitro, cyano, trifluoromethyl, oxo, $(C_1-C_6)$alkyl, —$OR_6$, —$NR_6R_7$, —$COR_6$, —$CO_2R_6$, —CONHOH, —$CONR_6R_7$, —$S(O)_mR_6$, —$S(O)_m$—$NR_6R_7$, —$NR_6COR_7$, —$NR_6SO_2R_7$, —$N(SO_2R_7)_2$, —$NR_6$—CO—$NR_7R_8$, and tetrazolyl, wherein:

m is an integer from 0 to 2 inclusive, $R_6$ and $R_7$ are identical or different and independently of each other are a hydrogen atom or a group of formula —$X_2$—$R_b$ wherein:

$X_2$ is a single bond or a $(C_1-C_6)$alkylene group, $R_b$ is a group, selected from $(C_1-C_6)$alkyl, cycloalkyl, heterocycloalkyl, aryl and heteroaryl, these groups being optionally substituted by 1 to 3 groups, identical or different, selected independently of each other from hydroxy, $(C_1-C_6)$alkoxy, $(C_1-C_6)$alkyl, amino, mono$(C_1-C_6)$alkylamino, di$(C_1-C_6)$alkylamino (each alkyl amino being identical or different, independently of each other), carboxy, $(C_1-C_6)$alkoxycarbonyl, and benzyl, $R_8$ is a hydrogen atom or a $(C_1-C_6)$alkyl group;

a racemic form thereof, an isomer thereof, an N-oxide thereof or a pharmaceutically acceptable acid or base salt thereof.

9. A compound of claim 1 wherein $R_3$ is a phenyl group substituted by one to three groups, identical or different, selected independently of each other from halogen, —$OR_6$, —$CO_2R_6$, —$CONR_6R_7$, —$S(O)_mR_6$, —$S(O)_m$—$NR_6R_7$, —$NR_6COR_7$ and tetrazolyl, wherein:

m is an integer from 0 to 2 inclusive, $R_6$ and $R_7$ are identical or different and independently of each other are a hydrogen atom or a group of formula —$X_2$—$R_b$ wherein:

$X_2$ is a single bond or a $(C_1-C_6)$alkylene group, $R_b$ is a group selected from $(C_1-C_6)$alkyl, cycloalkyl, heterocycloalkyl, aryl and heteroaryl, these groups being optionally substituted by 1 to 3 groups, identical or different, selected independently of each other from hydroxy, $(C_1-C_6)$alkoxy, $(C_1-C_6)$alkyl, amino, mono$(C_1-C_6)$alkylamino, di$(C_1-C_6)$alkylamino (each alkyl amino being identical or different, independently of each other), carboxy, $(C_1-C_6)$alkoxycarbonyl, and benzyl, a racemic form thereof, an isomer thereof, an N-oxide thereof or a pharmaceutically acceptable acid or base salt thereof.

10. A compound of claim 1 wherein $R_3$ is a group selected from quinoxalinyl, 1H-quinoxalinyl-2-one, quinazolinyl, 3H-quinazolinyl-4-one, and 1H-quinazolinyl-2,4-dione, which are optionally substituted by one to three groups, identical or different, selected independently of each other from halogen, $(C_1-C_6)$alkyl, —$OR_6$, and —$NR_6R_7$, wherein:

$R_6$ and $R_7$ are identical or different and independently of each other are a hydrogen atom or a group of formula —$X_2$—$R_b$ wherein:

$X_2$ is a single bond, $R_b$ is a group $(C_1-C_6)$alkyl, which is optionally substituted by one group selected from hydroxy, $(C_1-C_6)$alkoxy, amino, mono$(C_1-C_6)$alkylamino, and di$(C_1-C_6)$alkylamino (each alkyl amino being identical or different, independently of each other), a racemic form thereof, an isomer thereof, an N-oxide thereof or a pharmaceutically acceptable acid or base salt thereof.

11. A compound of claim 1 wherein:

$R_{1a}$ is a hydrogen atom, $R_{1b}$ is a cyclohexyl group optionally substituted by one hydroxy group, or a phenyl group optionally substituted by one tetrazolyl group or one —$CO_2R_4$ group in which $R_4$ represents a hydrogen atom or a $(C_1-C_6)$alkyl group, $R_2$ is a methyl group, $R_3$ is a phenyl group substituted by one to three groups, identical or different, selected independently of each other from halogen, —$OR_6$, —$CO_2R_6$, —$CONR_6R_7$, —$S(O)_mR_6$, —$S(O)_m$—$NR_6R_7$, —$NR_6COR_7$, and tetrazolyl, wherein:

m is an integer from 0 to 2 inclusive, $R_6$ and $R_7$ are identical or different and independently of each other are a hydrogen atom or a group of formula —$X_2$—$R_b$ wherein:

$X_2$ is a single bond or a $(C_1-C_6)$alkylene group, $R_b$ is a group selected from $(C_1-C_6)$alkyl, cycloalkyl, heterocycloalkyl, aryl and heteroaryl, these groups being optionally substituted by 1 to 3 groups, identical or different, selected independently of each other from hydroxy, $(C_1-C_6)$alkoxy, $(C_1-C_6)$alkyl, amino, mono$(C_1-C_6)$alkylamino, di$(C_1-C_6)$alkylamino (each alkyl amino being identical or different, independently of each other), carboxy, $(C_1-C_6)$alkoxycarbonyl, and benzyl, a racemic form thereof, an isomer thereof, an N-oxide thereof or a pharmaceutically acceptable acid or base salt thereof.

12. A compound of claim 1 wherein:

$R_{1a}$ is a hydrogen atom, $R_{1b}$ is a cyclohexyl group optionally substituted by one hydroxy group or a phenyl group optionally substituted by one tetrazolyl group or one —CO$_2$R$_4$ group in which R$_4$ represents a hydrogen atom or a (C$_1$–C$_6$)alkyl group, R$_2$ is a methyl group, R$_3$ is a group selected from quinoxalinyl, 1H-quinoxalinyl-2-one, quinazolinyl, 3H-quinazolinyl-4-one, 1H-quinazolinyl-2,4-dione, which are optionally substituted by one to three groups, identical or different, selected independently of each other from halogen, (C$_1$–C$_6$)alkyl, —OR$_6$, and —NR$_6$R$_7$, wherein R$_6$ and R$_7$ are identical or different and independently of each other are a hydrogen atom or a group of formula —X$_2$—R$_b$ wherein:

X$_2$ is a single bond,

R$_b$ is a (C$_1$–C$_6$)alkyl group, which is optionally substituted by one group selected from hydroxy, (C$_1$–C$_6$)alkoxy, amino, mono(C$_1$–C$_6$)alkylamino, and di(C$_1$–C$_6$)alkylamino (each alkyl amino being identical or different, independently of each other), a racemic form thereof, an isomer thereof, an N-oxide thereof or a pharmaceutically acceptable acid or base salt thereof.

13. A compound of claim 1 which is:

N-{4-[5-(cyclohexylamino)-4-methyl-1,3-thiazol-2-yl]phenyl}acetamide;

N-{4-[5-[(3-hydroxycyclohexyl)amino]-4-methyl-1,3-thiazol-2-yl]phenyl}acetamide;

7-[5-(cyclohexylamino)-4-methyl-1,3-thiazol-2-yl]quinazolin-4-amine; or

7-{5-[(3-hydroxycyclohexyl)amino]-4-methyl-1,3-thiazol-2-yl}quinazolin-4-amine; a racemic form thereof, an isomer thereof or a pharmaceutically acceptable acid or base salt of said compound, racemic form or isomer.

14. A process for preparing a compound of claim 1 wherein it is used as starting material a compound of formula (II):

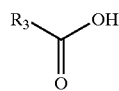

(II)

wherein R$_3$ is as defined in the compound of formula (I), compound of formula (II) reacting under peptidic coupling conditions with a compound of formula (III):

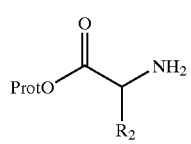

(III)

wherein R$_2$ is as defined in the compound of formula (I), and Prot represents a protective group of a carboxylic group, to give the compound of formula (IV):

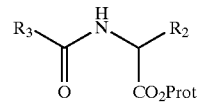

(IV)

wherein R$_2$, R$_3$ and Prot are as defined hereinbefore, compound of formula (IV) being deprotected in a first step by treatment with an acid or a base depending on the nature of the protecting group, to give the corresponding free carboxylic acid compound of formula (V):

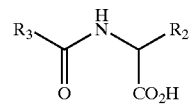

(V)

wherein R$_2$ and R$_3$ are as defined hereinbefore, and then in a second step reacting in peptidic coupling condition, in the presence of a coupling agent and a primary amine of formula (VI):

R$_{1b}$—NH$_2$ (VI)

wherein R$_{1b}$ is as defined in the compound of formula (I), to give the compound of formula (VII):

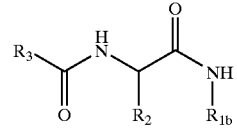

(VII)

wherein R$_{1b}$, R$_2$ and R$_3$ are as defined hereinbefore, compound of formula (VII) being treated with Lawesson's reagent in basic medium, to give the compound of formula (I/a), which is a particular case of the compounds of formula (I):

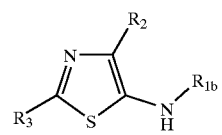

(I/a)

in which R$_{1b}$, R$_2$ and R$_3$ are as defined hereinbefore, compound of formula (I/a) being treated optionally under alkaline medium, with a compound of formula (VIII):

R$_{1a'}$—L$_1$ (VIII)

wherein R$_{1a'}$ has the same definition of the group R$_{1a}$ in the compound of formula (I) except the hydrogen atom definition, and L$_1$ represents a leaving group, to give the compound of formula (I/b) which is a particular case of the compound of formula (I):

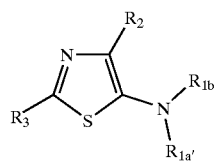

(I/b)

in which $R_{1a'}$, $R_{1b}$, $R_2$ and $R_3$ are as defined hereinbefore, compounds of formulae (I/a) and (I/b) constitute compounds of the invention, which are purified, where appropriate, according to a conventional purification technique, which are separated, where appropriate, into their different isomers according to a conventional separation technique, and which are converted, where appropriate, into addition salts thereof with a pharmaceutically acceptable acid or base, or into N-oxide thereof.

15. A pharmaceutical composition comprising a compound of claim 1 alone or in combination with one or more pharmaceutically acceptable excipients or carriers.

16. A method of treating a disease which is treatable by inhibition of PDE7 in a mammal, said method comprising administering to said mammal an effective amount of a compound of claim 1 or a pharmaceutical composition comprising a compound of claim 1 and one or more pharmaceutically acceptable excipients or carriers.

17. A method of claim 16 in which the disease to be treated is a T-cell-related disease, an autoimmune disease, an inflammatory disease, a respiratory disease, a CNS disease, an allergic disease, an endocrine or exocrine pancreas disease, a fertility disease or a gastrointestinal disease.

18. A method of claim 16 in which the disease to be treated is visceral pain, inflammatory bowel disease, osteoarthritis, multiple sclerosis, osteoporosis, chronic obstructive pulmonary disease (COPD), allergic rhinitis, asthma, cancer, acquired immune deficiency syndrome (AIDS) or graft rejection.

19. A method of claim 18 in which the disease to be treated is chronic pulmonary obstructive disease (COPD), allergic rhinitis or asthma.

* * * * *